United States Patent [19]

Murai et al.

[11] 3,991,186

[45] Nov. 9, 1976

[54] STERYL-β-D-GLUCOSIDE ESTER PHARMACEUTICAL COMPOSITIONS AND METHOD OF USE

[75] Inventors: Hiromu Murai; Koji Kitaguchi; Tatsuo Suminokura; Akira Sano; Massahiro Kise; Masahiko Kitano; Toshio Tomita, all of Kyoto, Japan

[73] Assignee: Nippon Shinyaku Co., Ltd., Kyoto, Japan

[22] Filed: Aug. 8, 1975

[21] Appl. No.: 603,085

[30] Foreign Application Priority Data

Aug. 14, 1974 Japan.............................. 49-93623

[52] U.S. Cl..................................... 424/182; 536/5
[51] Int. Cl.².......................................... C07J 19/00
[58] Field of Search................... 260/210.5; 424/182

[56] References Cited

UNITED STATES PATENTS

| | | | |
|---|---|---|---|
| 2,415,301 | 2/1947 | Mattikow........................ | 260/210.5 |
| 3,347,848 | 10/1967 | Ismail et al...................... | 260/234 R |
| 3,480,616 | 11/1969 | Osipow et al................... | 260/234 R |

FOREIGN PATENTS OR APPLICATIONS 1,298,047  11/1972  United Kingdom............. 260/210.5

*Primary Examiner*—Johnnie R. Brown

[57] ABSTRACT

Steryl-6-O-palmitoyl and -2,3,4,6-O-tetrapalmitoyl-β-D-glucosides are anti-inflammatory agents. The compounds, of which β-sitosteryl-2,3,4,6-O-tetrapalmitoyl-β-D-glucoside is a representative embodiment, are prepared through the reaction of a steryl-β-D-glucoside with a lower alkyl ester of palmitic acid in the presence of a basic catalyst.

2 Claims, No Drawings

STERYL-β-D-GLUCOSIDE ESTER PHARMACEUTICAL COMPOSITIONS AND METHOD OF USE

DETAILED DESCRIPTION

The present invention pertains to steryl-6-0-palmitoyl-β-D-glucosides and steryl-2,3,4,6,-0-tetrapalmitoyl-β-D-glucosides, their use as anti-inflammatory agents, and methods for their preparation.

The compounds prepared according to the present invention can be diagrammatically depicted by the formula:

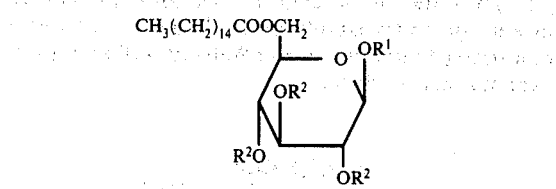

wherein $R^1$ is a steroid group selected from the group consisting of β-sitosteryl, campesteryl, stigmasteryl or cholesteryl and $R^2$ is hydrogen or palmitoyl.

The foregoing compounds obtained in accordance with this invention exhibit strong anti-inflammatory effects with an exceptionally low toxicity. They are accordingly extremely useful as pharmaceuticals, in particular for use in effecting an anti-inflammatory response in humans and animals through administration of an anti-inflammatory effective amount of the compound.

The compounds are prepared by treating a β-D-glucoside of said steroid with an alkyl ester of palmitic acid. Suitable esters include those of 1 to 6 carbon atoms such as methyl, ethyl, propyl, isopropyl, butyl and the like. The reaction is conducted with or without a solvent. Suitable solvents include for example N,N-dimethylformamide, dimethylsulfoxide, dioxane, and the like. Moreover, the reaction is conducted in the presence of a base such as an alkali metal salt, alkali metal alkoxide, and the like, generally with the application of external heat. An excess of the lower alkyl palmitate is employed. When a small excess, e.g. a 4-fold excess, is employed, the product is primarily the monoester. When a large excess, e.g. a 20-fold excess, is employed, the product is predominately the tetraester.

The steryl-β-D-glucosides can be isolated from lecithin according to known methods and are in general commercially available. From an economic point of view, it is particularly attractive to utilize commercially available β-sitosteryl which is approximately 60% in purity and contains the β-D-glucosides of campesterol, stigmasterol and related sterols. Likewise, one may use the commercially available β-D-glucosides of cholesterol, campesterol and the like. It is generally unnecessary to isolate the individual steryl components of these β-D-glucosides and the mixtures may be used as such, both in the preparation of the anti-inflammatory product and its eventual use.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The potent anti-inflammatory properties of the present compounds and the exceptionally low toxicity can be conveniently observed in well known and widely accepted laboratory models. For example, the anti-inflammatory properties are apparent in the carrageenin-induced rat paw edema method in which a significant anti-inflammatory effect is observed as much as five hours after intraperitoneal injection of doses as low as 10 mg/kg. The overall pattern of anti-inflammatory effects can be seen from the following data:

Table I

| Inhibitory Effect of Carrageenin-Induce Edema (Paw Edema Method in Rats) | | | | | |
|---|---|---|---|---|---|
| I.P. Dose | % Inhibition | | | | |
| (mg/kg) | 1 hr | 2 hrs | 3 hrs | 4 hrs | 5 hrs |
| 10 | −3.7 | 13.2 | 26.6 | 37.1 | 24.9 |
| 20 | 24.2 | 37.6 | 41.6 | 42.8 | 28.1 |

The $LD_{50}$ in mice for these compounds is greater than 3,000 mg/kg upon either intraperitoneal or oral administration, in both male and female animals.

The following examples will serve to further typify the nature of the present invention but should not be construed as a limitation on the scope thereof, the scope being defined solely by the appended claims.

EXAMPLE 1

A mixture of 165.7 g of steryl-β-D-glucoside, 312 g of methyl palmitate, and 40 g of potassium carbonate and 1.2 liters of N,N-dimethylformamide is heated at 120° C. with agitation. During the reaction, the reactor is evacuated for 5 minutes every two hours to remove the methanol being formed. The reaction is stopped after 20 hours and the N,N-dimethylformamide is removed under reduced pressure. Benzene (1 liter) is added to the residue and the crystals which separate upon cooling are collected by filtration. The benzene solution is passed through a column, 8 cm in diameter and 50 cm in length, packed with 500 g of silica gel (Wakogel C-200) and the column is further eluted with a 1:1 mixture of benzene and ether to collect fractions containing steryl-6-O-palmitoyl-β-D-glucoside. The yield is 56 g. The product of extremely high purity is obtained in a yield of 46 g after recrystallization from ethanol; melting point, 120°–190° C.

Elementary analysis calculated for $C_{51}H_{90}O_7$:
C, 75.13; H, 11.13.
Found: C, 75.66; H, 10.87.

EXAMPLE 2

A mixture of 1 g of steryl-β-D-glucoside, 10 g of isopropyl palmitate and 1 g of potassium carbonate is heated with agitation at 150°–160° C for 4 hours without solvent. After completion of the reaction, the procedure of Example 1 was followed to obtain 1 g of steryl-2,3,4,6-O-tetrapalmitoyl-β-D-glucoside. After recrystallization from ethanol, the product melts at 78°–81° C.

Elementary analysis calculated for $C_{99}H_{180}O_{10}$:
C, 77.69; H, 11.86.
Found: C, 77.89; H, 11.60.

What is claimed is:

1. The method of effecting an anti-inflammatory response in animals and humans which comprises administering thereto an anti-inflammatory amount of a compound of the formula:

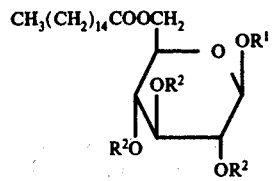

wherein $R^1$ is a steroid group selected from the group consisting of β-sitosteryl, campesteryl, stigmasteryl or cholesteryl and $R^2$ is palmitoyl.

2. A pharmaceutical composition comprising an anti-inflammatory effective amount of a compound of the formula:

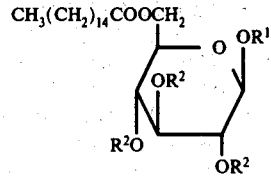

wherein $R^1$ is a steroid group selected from the group consisting of β-sitosteryl, campesteryl, stigmasteryl or cholesteryl and $R^2$ is palmitoyl, and a pharmaceutically acceptable carrier.

* * * * *